(12) United States Patent
Ferreira

(10) Patent No.: US 8,876,710 B2
(45) Date of Patent: Nov. 4, 2014

(54) SURGICAL PORTAL APPARATUS WITH EXPANDABLE CANNULA

(75) Inventor: Daniel P. Ferreira, Milford, CT (US)

(73) Assignee: Covidien LP, Mansfield, MA (US)

( * ) Notice: Subject to any disclaimer, the term of this patent is extended or adjusted under 35 U.S.C. 154(b) by 728 days.

(21) Appl. No.: 12/724,884

(22) Filed: Mar. 16, 2010

(65) Prior Publication Data

US 2010/0256452 A1 Oct. 7, 2010

Related U.S. Application Data

(60) Provisional application No. 61/167,175, filed on Apr. 7, 2009.

(51) Int. Cl.
*A61B 1/32* (2006.01)
*A61B 17/34* (2006.01)

(52) U.S. Cl.
CPC ......... *A61B 17/3439* (2013.01); *A61B 17/3431* (2013.01)
USPC ...................................................... 600/206

(58) Field of Classification Search
USPC ............ 600/114, 115, 164.03, 164.1, 164.11, 600/206, 207; 604/104, 523–527; 606/198
See application file for complete search history.

(56) References Cited

U.S. PATENT DOCUMENTS

| | | | |
|---|---|---|---|
| 3,509,883 A | 5/1970 | Dibelius | |
| 3,788,318 A | 1/1974 | Kim et al. | |
| 3,815,608 A * | 6/1974 | Spinosa et al. | 604/105 |
| 3,968,800 A | 7/1976 | Vilasi | |
| 4,899,729 A | 2/1990 | Gill et al. | |
| 5,139,511 A | 8/1992 | Gill et al. | |
| 5,312,417 A | 5/1994 | Wilk | |
| 5,431,676 A | 7/1995 | Dubrul et al. | |
| 5,584,850 A * | 12/1996 | Hart et al. | 606/185 |
| 5,637,091 A * | 6/1997 | Hakky et al. | 604/96.01 |
| 5,674,240 A | 10/1997 | Bonutti et al. | |
| 5,735,867 A * | 4/1998 | Golser et al. | 606/185 |
| 5,814,073 A | 9/1998 | Bonutti | |
| 5,944,691 A | 8/1999 | Querns et al. | |
| 6,228,053 B1 | 5/2001 | Morse | |
| 6,283,972 B1 * | 9/2001 | Riley | 606/81 |

(Continued)

FOREIGN PATENT DOCUMENTS

| | | |
|---|---|---|
| EP | 1454590 | 9/2004 |
| WO | WO 02/051323 A1 | 7/2002 |
| WO | WO 03/011154 A2 | 2/2003 |

*Primary Examiner* — Christian Sevilla

(57) ABSTRACT

A surgical portal apparatus includes a housing and a portal member extending from the housing. The portal member is dimensioned for insertion within tissue to access an underlying tissue site and defines a longitudinal axis. The portal member includes an outer wall having a longitudinal opening for reception of a surgical object. The outer wall includes first and second peripheral segments extending along the longitudinal axis. The first peripheral segment includes a substantially rigid material and the second peripheral segment includes a substantially elastomeric material. The first peripheral segment and the second peripheral segment cooperate to permit the outer wall to radially expand from a first condition where the outer wall defines a first internal dimension to a second condition where the outer wall defines a second internal dimension greater than the first internal dimension upon insertion of the surgical object.

19 Claims, 2 Drawing Sheets

(56) References Cited

U.S. PATENT DOCUMENTS

| | | |
|---|---|---|
| 6,312,443 B1 | 11/2001 | Stone |
| 6,613,038 B2 * | 9/2003 | Bonutti et al. ............... 604/509 |
| 6,811,558 B2 | 11/2004 | Davison et al. |
| 6,814,715 B2 | 11/2004 | Bonutti et al. |
| 7,854,109 B2 * | 12/2010 | Zubiate et al. ............... 59/78.1 |
| 2004/0049099 A1 * | 3/2004 | Ewers et al. ............... 600/206 |
| 2004/0087968 A1 | 5/2004 | Core |
| 2007/0051375 A1 | 3/2007 | Milliman |

* cited by examiner

SURGICAL PORTAL APPARATUS WITH EXPANDABLE CANNULA

BACKGROUND

1. Technical Field

The present disclosure relates to a surgical portal apparatus adapted to permit the introduction of surgical instrumentation into a patient's body in sealing engagement therewith. In particular, the present disclosure is directed to a surgical portal apparatus having an expandable cannula adapted to permit the introduction of a variety of different sized and shaped surgical objects.

2. Background of Related Art

In laparoscopic procedures surgery is performed in the interior of the abdomen through a small incision; in endoscopic procedures surgery is performed in any hollow viscus of the body through a narrow tube or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissue, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly made up of a cannula assembly and an obturator assembly. Since the cannula assembly provides a direct passage for surgical instrumentation from outside the patient's body to access internal organs and tissue, it is important that the cannula assembly maintain a relatively fluid-tight interface between the abdominal cavity and the outside atmosphere. The cannula assembly generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as $CO_2$ is introduced into the body cavity, thereby creating a pneumoperitoneum. The gas provides a positive pressure which raises the inner body wall away from internal organs, thereby providing the surgeon with a region within which to operate and avoiding unnecessary contact with the organs by the instruments inserted through the cannula assembly. An obturator of the obturator assembly is inserted into the cannula assembly and used to puncture the abdominal wall. Following removal of the obturator assembly from the cannula assembly, laparoscopic or endoscopic surgical instruments may be inserted through the cannula assembly to perform surgery within the abdominal cavity.

Without the obturator assembly to block the flow of insufflation gas out from the cavity, other structure must be provided to maintain a relatively fluid-tight interface between the abdominal cavity and the outside atmosphere. Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannulae required and facilitating efficiency in the surgical procedure. It is further desirable to maintain a seal about the instrument for manipulation of the instrument within the cannula assembly.

Although attempts have been made to provide a seal assembly as part of or for use in conjunction with a cannula assembly which maintains the integrity of the seal between the body cavity and the atmosphere outside the patient's body, seal systems provided to date have failed to address the full range of surgeons' needs.

SUMMARY

Accordingly, the present disclosure is directed to a surgical portal apparatus including a housing and a portal member extending from the housing. The portal member is dimensioned for insertion within tissue to access an underlying tissue site and defines a longitudinal axis. The portal member includes an outer wall having a longitudinal opening for reception of a surgical object. The outer wall includes first and second peripheral segments extending along the longitudinal axis. The first peripheral segment includes a substantially rigid material and the second peripheral segment includes a substantially elastomeric material. The first peripheral segment and the second peripheral segment cooperate to permit the outer wall to radially expand from a first condition where the outer wall defines a first internal dimension to a second condition where the outer wall defines a second internal dimension greater than the first internal dimension upon insertion of the surgical object.

The outer wall may include a plurality of first peripheral segments and a plurality of second peripheral segments. The first and second peripheral segments may be arranged in alternating radial relation relative to the longitudinal axis. The first and second peripheral segments each may extend along the longitudinal axis for at least a majority of the length of the portal member. A connector segment may be disposed between the housing and the portal member. The connector segment may comprise an elastomeric material. The connector segment may be adapted for displacement upon movement of the outer wall from the first condition to the second condition. The connector segment may be dimensioned to restrict passage of the portal member within the tissue when displaced and when the outer wall is in the second condition.

The first peripheral segments may be substantially equidistally radially spaced and the second peripheral segments may be substantially equidistally radially spaced. At least three or four first peripheral segments and at least three or four second peripheral segments may be provided.

Each first peripheral segment may include a rib extending radially inwardly towards the longitudinal axis. The ribs may be positioned to contact the surgical object to facilitate expansion of the outer wall from the first condition to the second condition. The ribs of adjacent first peripheral segments may define pathways for passage of insufflation gas through the portal member. The ribs of adjacent first peripheral segments may be dimensioned to substantially align the surgical object with the longitudinal axis. The housing may include an insufflation inlet port in communication with the pathways.

A zero closure valve may be included to close the longitudinal opening in the absence of the surgical object. An object seal may be included to intersect the longitudinal axis and is adapted to establish a substantial seal about the surgical object.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 2:
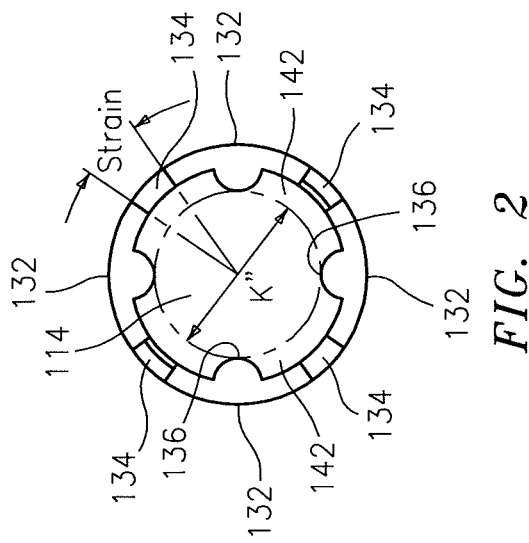
FIG. 2 is an axial cross sectional view of the surgical portal apparatus of FIG. 1.

The surgical portal apparatus of the present disclosure provides a substantial seal between a body cavity of a patient and the outside atmosphere before, during and after insertion and manipulation of a surgical instrument through the seal thereof.

The surgical portal apparatus of the present disclosure contemplates the introduction and manipulation of various types of instrumentation adapted for insertion through a trocar and/or cannula assembly while maintaining a substantially fluid-tight interface about the instrument to preserve the atmospheric integrity of a surgical procedure from leakage. Examples of instrumentation include, but are not limited to, clip appliers, graspers, dissectors, retractors, staplers, laser probes, photographic devices, endoscopes and laparoscopes, tubes, and the like. Furthermore, these surgical instruments can be designed with a variety of tip configurations and a variety of diameters. Such instruments will collectively be referred to as "instruments" or "instrumentation" or "surgical objects."

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Figure 1:
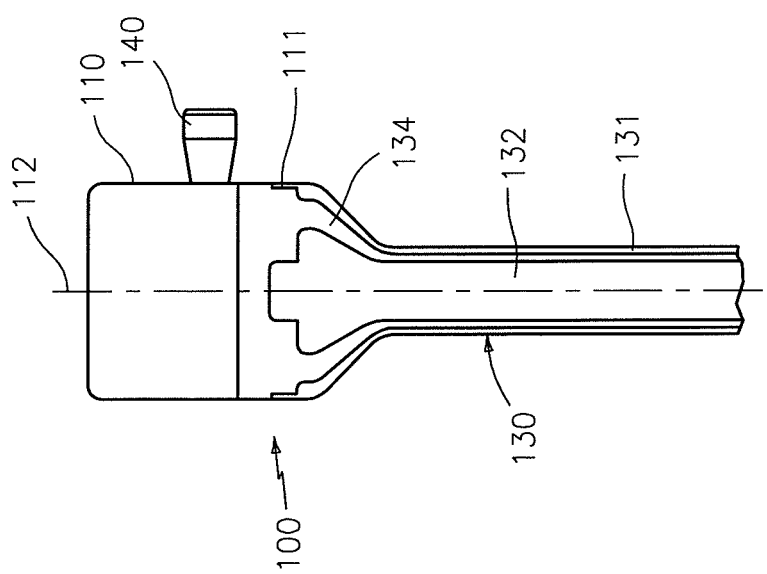
FIG. 1 is a side elevational view of a surgical portal apparatus in a first condition in accordance with the present disclosure.
Figure 3:
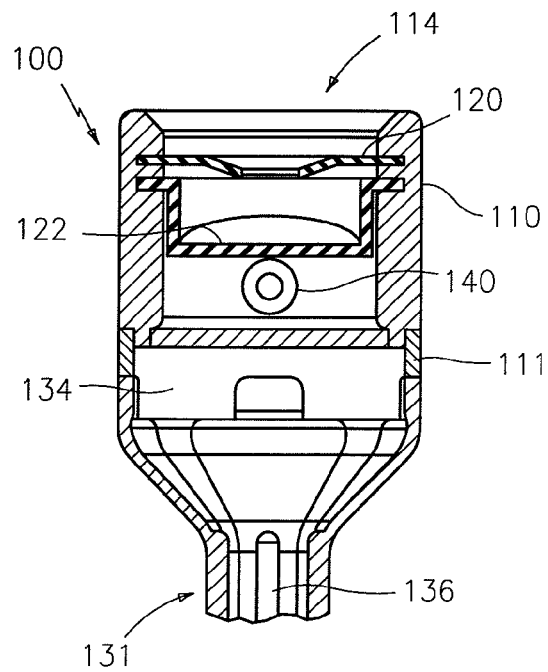
FIG. 3 is a side cross sectional view of the housing of the surgical portal apparatus of FIGS. 1 and 2.

Referring now to the drawings, in which like reference numerals identify identical or substantially similar parts throughout the several views, FIGS. 1-3 and FIG. 4 illustrate a surgical portal apparatus 100. In accordance with the present disclosure, the surgical portal apparatus 100 includes a housing 110, an object seal 120, and a portal member 130. The portal member 130 extends from the housing 110 and is dimensioned for insertion within tissue to access an underlying tissue site. The portal member 130 defines a longitudinal axis 112 (FIG. 1). The portal member 130 and the housing 110 have a longitudinal opening 114 (FIGS. 1 and 3) for reception of a surgical object "I." As shown in FIG. 3, an object seal 120 is disposed in mechanical cooperation with the housing 110 and defines a passage for reception of a surgical object "I" (FIG. 4) in substantial sealed relation therewith. More specifically, the object seal 120 intersects the longitudinal axis 112 and is adapted to establish a substantial seal about the surgical object "I." A zero closure valve 122 (FIG. 3), (e.g., a duckbill valve) can also be disposed in mechanical cooperation with the housing 110. The zero closure valve 122 is adapted to close the longitudinal opening 114 in the absence of the surgical object "I."

Figure 4:
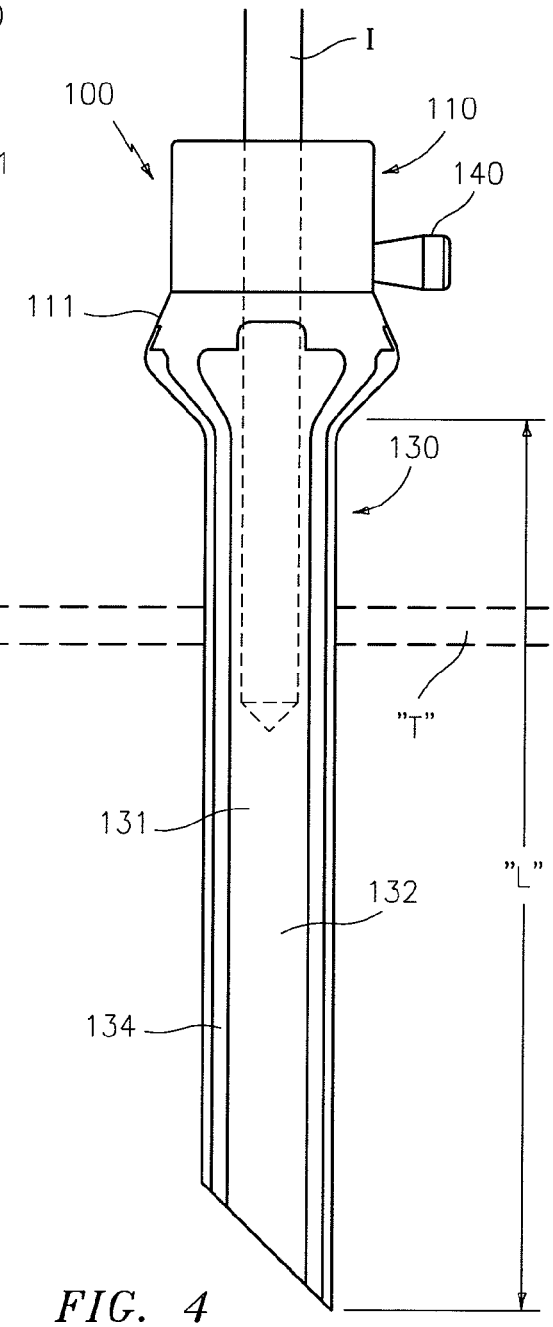
FIG. 4 is a side elevational view of the surgical portal apparatus of FIGS. 1-3 in a second condition.

As shown in FIGS. 1 and 4, portal apparatus 100 includes connector segment 111 which connects the housing 110 with portal member 130. Connector segment 111 is generally annular in configuration and, in one embodiment, is fabricated from an elastomeric material. Connector segment 111 may be secured to housing 110 and portal member 130 through conventional means. Connector segment 111 is adapted to transition from a first generally parallel and concentric arrangement with respect to the longitudinal axis 112 (FIG. 2) to a second angulated or tapered arrangement with respect to the longitudinal axis (FIG. 4) during transition of the apparatus 100 as discussed hereinbelow in greater detail.

With continued reference to FIGS. 1-2, portal member 130 includes outer wall 131. Outer wall 131 includes at least one first peripheral segment 132, and at least one second peripheral segment 134. In one embodiment, at least three, and possibly, four first peripheral segments 132 are provided and, at least three, possibly, four second peripheral segments 134 are provided. In one embodiment, first peripheral segments 132 and second peripheral segments 134 are arranged in alternating radial relation relative to the longitudinal axis 112 and extend along the longitudinal axis 112. Each first peripheral segment portion 132 may be substantially equidistally radially spaced about the longitudinal axis. Similarly, second peripheral segment portions 134, etc. may be substantially equidistally radially spaced about the longitudinal axis 112.

Each first peripheral segment 132 may be fabricated at least in part from a substantially rigid material and each second peripheral segment 134 may be fabricated at least in part from a substantially elastomeric material. Suitable rigid materials include steel, titanium, aluminum or rigid polymeric materials. Suitable elastomeric materials include natural rubber, polyisoprene or any other suitable elastomeric material. First and second peripheral segments 132, 134 may extend along the longitudinal axis 112 for at least a majority of the length "l" of the portal member 130. Second peripheral segments 134 may be integrally and/or monolithically formed with connector segment 111 for example during a molding process. In addition, it is envisioned that second peripheral segments 134 and connector segment 111 may be molded as a single unit and subsequently connected to housing 110 and first peripheral segments via an over molding process to connect the components.

First peripheral segments 132, second peripheral segments 134 and, optionally connector segment 111, cooperate to permit the outer wall 131 to radially expand from a first condition where the outer wall 131 defines a first internal dimension to a second condition where the outer wall 131 defines a second internal dimension greater than the first internal dimension upon insertion of the surgical object "I."

At least one, e.g., or all first peripheral segments 132, or portions thereof, may include at least one radially inwardly (towards the longitudinal axis 112) protruding rib 136. Each rib 136 is positioned to contact the surgical object "I" to facilitate expansion of the outer wall 131 from the first condition to the second condition. A plurality of inwardly protruding ribs 136 are shown disposed about the longitudinal axis 112. Each inwardly protruding rib 136 is configured and dimensioned to contact and guide surgical objects "I" disposed therein down the portal member 130.

With reference to FIG. 4, each second peripheral segment 134 is configured and dimensioned to expand to permit outer wall 131 to expand to the second internal dimension. In one embodiment, about 300 percent circumferential strain is required to expand outer wall 131 to the second internal dimension. The degree or level of strain may be altered or modified by varying the ratio of rigid and elastomeric materials constituting the first and second peripheral segments 132, 134, respectively. Each second peripheral segment 134 may avoid contact with the surgical objects "I" disposed therein. Furthermore, during transition from the first condition to the second condition, connector segment 111 may displace to become angulated or obliquely arranged (e.g., tapered) to the longitudinal axis 112 to accommodate the expansion of second peripheral segments 134. Connector segment 111, in the condition of FIG. 4, may also function as an anchor to engage the body tissue "t" (in phantom) thereby preventing over insertion of the portal apparatus 100.

Referring again to FIGS. 1 and 4, the portal member 130 is configured and dimensioned to be expandable from a first condition (FIG. 1) having a diameter of about 4.5 mm to a second condition (FIG. 4) having a diameter of about 12.5 mm. Other dimensions are also envisioned. The portal member 130 includes an internal dimension "K" defined by the internal surface thereof. The internal dimension 113 is configured and dimensioned to radially expand from the first condition to the second condition. Thus, the portal member 130 can accommodate a plurality of different surgical objects "I" during the reception and manipulation thereof. Furthermore, by virtue of at least protruding ribs 136, the portal member 130 is configured and dimensioned to inhibit surgical objects "I" from angling away from the longitudinal axis 112 during the manipulation of each surgical object "I" disposed within the portal member 130. For example, the protruding ribs 136 assist in maintaining concentricity of the instrument "I" with respect to the longitudinal axis 112.

Referring additionally to FIGS. 1, 3, and 4, the housing 110 further includes an insufflation inlet port 140 disposed thereon. As illustrated in FIG. 4, also contemplated is a plurality of pathways 142 disposed in fluid communication with the insufflation inlet port 140. The plurality of pathways 142 are circumferentially disposed about the longitudinal axis 112 between adjacent inwardly protruding ribs 136. In other words, the ribs 136 of adjacent first peripheral segments 132 define pathways 142 for passage of insufflation gas through the portal member 130. The pathways 142 are in fluid communication with the insufflation port 140.

In use, a surgical object "I" is inserted into the housing 110 and passed through the object seal 120 and the zero closure valve 122 and into the internal dimension 113 of the portal member 130. If the surgical object "I" has a dimension that exceeds the diameter of the outer wall 131 in the first condition (FIG. 1) of the portal member 130, the object contacts the ribs 136 and applied forces causing expansion of the second peripheral segments 134 and transitioning of the connector segment 111 whereby the portal member 130 assumes the second condition (FIG. 4) in order to accommodate the surgical object "I". The ribs 136 assist in biasing the object "I" towards a generally aligned position with respect to the longitudinal axis 112. Upon withdrawal of the surgical object "I" from the portal member 130, the second peripheral segments 134 and connector segment 111 return, under the normal resiliency of their material of fabrication, to the first condition (FIG. 1).

While several embodiments of the disclosure have been shown in the drawings, it is not intended that the disclosure be limited thereto, as it is intended that the disclosure be as broad in scope as the art will allow and that the specification be read likewise. For example, portal apparatus 100 may be adapted for reception of a hand of a surgeon during, e.g., a hand assisted laparoscopic procedure. Therefore, the above description should not be construed as limiting, but merely as exemplifications preferred embodiments. Thus the scope of the embodiments should be determined by the appended claims and their legal equivalents, rather than by the examples given.

What is claimed is:

1. A surgical portal apparatus, which comprises:
   a housing; and
   a portal member extending from the housing, the portal member dimensioned for insertion within tissue to access an underlying tissue site and defining a longitudinal axis, the portal member including an outer wall having a longitudinal opening for reception of a surgical object, the outer wall including first and second peripheral segments extending along the longitudinal axis, the first and second peripheral segments being externally exposed to form an external surface of the outer wall, the first peripheral segment including a substantially rigid material and the second peripheral segment including a substantially elastomeric material, the first peripheral segment and the second peripheral segment cooperating to permit the outer wall to radially expand from a first condition where the outer wall defines a first internal dimension to a second condition where the outer wall defines a second internal dimension greater than the first internal dimension upon insertion of the surgical object.

2. The surgical portal apparatus according to claim 1 wherein the outer wall includes a plurality of first peripheral segments and a plurality of second peripheral segments, the first and second peripheral segments being arranged in alternating radial relation relative to the longitudinal axis.

3. The surgical portal apparatus according to claim 2 wherein the first and second peripheral segments each extend along the longitudinal axis for at least a majority of the length of the portal member.

4. The surgical portal apparatus according to claim 3 including a connector segment disposed between the housing and the portal member, the connector segment comprising an elastomeric material.

5. The surgical portal apparatus according to claim 4 wherein the connector segment is adapted for displacement upon movement of the outer wall from the first condition to the second condition.

6. The surgical portal apparatus according to claim 5 wherein the connector segment is dimensioned to restrict passage of the portal member within the tissue when the outer wall is in the second condition.

7. The surgical portal apparatus according to claim 3 wherein the first peripheral segments are substantially equidistally radially spaced.

8. The surgical portal apparatus according to claim 7 wherein the second peripheral segments are substantially equidistally radially spaced.

9. The surgical portal apparatus according to claim 1 including at least three first peripheral segments and at least three second peripheral segments.

10. The surgical portal apparatus according to claim 1 including at least four first peripheral segments and at least four second peripheral segments.

11. A surgical portal apparatus according to claim 2 wherein each first peripheral segment includes a rib extending radially inwardly towards the longitudinal axis, the rib positioned to contact the surgical object to facilitate expansion of the outer wall from the first condition to the second condition.

12. The surgical portal apparatus according to claim 11 wherein the ribs of adjacent first peripheral segments define pathways for passage of insufflation gas through the portal member.

13. The surgical portal apparatus according to claim 11 wherein the ribs of adjacent first peripheral segments are dimensioned to substantially align the surgical object with the longitudinal axis.

14. The surgical portal apparatus according to claim 12 wherein the housing includes an insufflation inlet port.

15. The surgical portal apparatus according to claim 2 including a zero closure valve adapted to close the longitudinal opening in the absence of the surgical object.

16. The surgical portal apparatus according to claim 2 including an object seal intersecting the longitudinal axis adapted to establish a substantial seal about the surgical object.

17. The surgical portal apparatus according to claim 1 wherein the first and second peripheral segments are equidistally radially spaced about the longitudinal axis.

18. The surgical portal apparatus according to claim 1 wherein the outer wall includes an internal surface that defines the longitudinal opening.

19. The surgical portal apparatus according to claim 18 wherein the outer wall has a thickness that is defined between the internal and external surfaces of the outer wall.

* * * * *